United States Patent
Young et al.

(10) Patent No.: US 7,195,764 B2
(45) Date of Patent: Mar. 27, 2007

(54) CANCEROUS DISEASE MODIFYING ANTIBODIES

(75) Inventors: David S. F. Young, Toronto (CA); Susan E. Hahn, Toronto (CA); Helen P. Findlay, Toronto (CA)

(73) Assignee: Arius Research Inc., Ontario (CA)

(*) Notice: Subject to any disclaimer, the term of this patent is extended or adjusted under 35 U.S.C. 154(b) by 0 days.

(21) Appl. No.: 10/944,664

(22) Filed: Sep. 15, 2004

(65) Prior Publication Data

US 2005/0053609 A1    Mar. 10, 2005

Related U.S. Application Data

(63) Continuation-in-part of application No. 10/413,755, filed on Apr. 14, 2003, now Pat. No. 6,794,494.

(51) Int. Cl.
  *A61K 39/395*  (2006.01)
  *C12P 21/04*   (2006.01)
  *C12P 21/08*   (2006.01)
  *C07K 16/00*   (2006.01)

(52) U.S. Cl. ............ 424/141.1; 424/133.1; 424/155.1; 424/181.1; 435/69.6; 435/70.21; 530/387.3; 530/388.1; 530/388.8; 530/391.7

(58) Field of Classification Search ............ 424/130.1, 424/133.1, 141.1, 143.1, 155.1, 181.1; 530/387.1, 530/387.3, 388.1, 388.8, 391.3, 391.7; 435/69.6, 435/70.21

See application file for complete search history.

(56) References Cited

U.S. PATENT DOCUMENTS

| | | | |
|---|---|---|---|
| 4,861,581 A | 8/1989 | Epstein et al. | |
| 5,171,665 A | 12/1992 | Hellstrom et al. | |
| 5,484,596 A | 1/1996 | Hanna, Jr. et al. | |
| 5,693,763 A | 12/1997 | Codington et al. | |
| 5,750,102 A | 5/1998 | Eisenbach et al. | |
| 5,780,033 A | 7/1998 | Torchilin et al. | |
| 5,783,186 A | 7/1998 | Arakawa et al. | |
| 5,849,876 A | 12/1998 | Linsley et al. | |
| 5,869,045 A | 2/1999 | Hellstrom et al. | |
| 5,869,268 A | 2/1999 | Kudo et al. | |
| 6,180,357 B1 | 1/2001 | Young et al. | |
| 6,657,048 B2 | 12/2003 | Young et al. | |
| 6,824,780 B1 * | 11/2004 | Devaux et al. | |
| 2004/0001789 A1 * | 1/2004 | Young et al. | |
| 2004/0105815 A1 * | 6/2004 | Young et al. | |
| 2004/0197328 A1 * | 10/2004 | Young et al. | |
| 2004/0258693 A1 * | 12/2004 | Young et al. | |
| 2005/0063967 A1 * | 3/2005 | Young et al. | |

FOREIGN PATENT DOCUMENTS

| WO | 2003/055515 | 7/2003 |
|---|---|---|
| WO | WO2004/089989 | 10/2004 |

OTHER PUBLICATIONS

Morrison et al. Proc. Natl. Acad. Sci. USA, 81:6851-6855, 1984.*
Campbell et al. Biology, 5th ed. p. 856, 1999.*
Co et al. Nature, 351(6):501-502, Jun. 6, 1991.*
Presta et al. Biochemical Society Transactions, 30(4):487-490, 2002.*
J. Berzoksky et al, "Chapter 8: Immunogenicity and antigen structure", in Fundamental Immunology, p. 242, ed. William E. Paul, M.D., 3d ed., Raven Press, NY (1993).
J. Desousa-Hitzler et al, "Functional approach to therapeutic antibody generation yields antibodies effective against relevant tumor antigens", Clinical Cancer Reserch, 9(16/2):6187S (Dec. 2003) Abstract.
H. Ishizuka et al, "Antitumour activity of murine monoclonal antibody NCC-ST-421 on human cancer cells by inducing apoptosis", Anticancer Research, 18:2513-2518 (1998).

* cited by examiner

*Primary Examiner*—Sheela J. Huff
*Assistant Examiner*—David J. Blanchard
(74) *Attorney, Agent, or Firm*—McHale & Slavin, P.A.

(57) ABSTRACT

The present invention relates to a method for producing patient cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, and hematogenous cells.

7 Claims, 3 Drawing Sheets

CANCEROUS DISEASE MODIFYING ANTIBODIES

REFERENCE TO RELATED APPLICATIONS

This application is a continuation-in-part of application Ser. No. 10/413,755, filed Apr. 14, 2003, now U.S. Pat. No. 6,794,494, issued Sep. 21, 2004, the contents of which is herein incorporated by reference.

FIELD OF THE INVENTION

This invention relates to the isolation and production of cancerous disease modifying antibodies (CDMAB) and to the use of these CDMAB in therapeutic and diagnostic processes, optionally in combination with one or more chemotherapeutic agents. The invention further relates to binding assays, which utilize the CDMAB of the instant invention.

BACKGROUND OF THE INVENTION

Each individual who presents with cancer is unique and has a cancer that is as different from other cancers as that person's identity. Despite this, current therapy treats all patients with the same type of cancer, at the same stage, in the same way. At least 30 percent of these patients will fail the first line of therapy, thus leading to further rounds of treatment and the increased probability of treatment failure, metastases, and ultimately, death. A superior approach to treatment would be the customization of therapy for the particular individual. The only current therapy that lends itself to customization is surgery. Chemotherapy and radiation treatment cannot be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells.

Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remissions or responses. Furthermore, there was a lack of reproducibility and no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least 4 clinical trials for human breast cancer, which produced only 1 responder from at least 47 patients using antibodies against specific antigens or based on tissue selectivity. It was not until 1998 that there was a successful clinical trial using a humanized anti-Her2 antibody in combination with cisplatin. In this trial 37 patients were accessed for responses of which about a quarter had a partial response rate and another half had minor or stable disease progression.

The clinical trials investigating colorectal cancer involve antibodies against both glycoprotein and glycolipid targets. Antibodies such as 17-1A, which has some specificity for adenocarcinomas, had undergone Phase 2 clinical trials in over 60 patients with only 1 patient having a partial response. In other trials, use of 17-1A produced only 1 complete response and 2 minor responses among 52 patients in protocols using additional cyclophosphamide. Other trials involving 17-1A yielded results that were similar. The use of a humanized murine monoclonal antibody initially approved for imaging also did not produce tumor regression. To date there has not been an antibody that has been effective for colorectal cancer. Likewise there have been equally poor results for lung, brain, ovarian, pancreatic, prostate, and stomach cancers. There has been some limited success in the use of an anti-GD3 monoclonal antibody for melanoma. Thus, it can be seen that despite successful small animal studies that are a prerequisite for human clinical trials, the antibodies that have been tested thus far, have been for the most part, ineffective.

Prior Patents:

U.S. Pat. No. 5,750,102 discloses a process wherein cells from a patient's tumor are transfected with MHC genes, which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas is not dependent upon the epithelial tissue of origin.

U.S. Pat. No. 5,783,186 is drawn to anti-Her2 antibodies, which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an anti-nuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal anti-nuclear autoantibody from an aged mammal, and a hybridoma cell line producing a monoclonal anti-nuclear autoantibody.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies, which are useful in treating a cancerous disease. For the purpose of this document, the terms "antibody" and "monoclonal antibody" (mAb) may be used interchangeably and refer to intact immunoglobulins produced by hybridomas (e.g. murine or human), immunoconjugates and, as appropriate, immunoglobulin fragments and recombinant proteins derived from immunoglobulins, such as chimeric and humanized immunoglobulins, F(ab') and F(ab')$_2$ fragments, single-chain antibodies, recombinant immunoglobulin variable regions (Fv)s, fusion proteins etc. For the purpose of this document, the term "tissue sample" is understood to mean at least one cell or an aggregate of cells obtained from a mammal. It is well recognized in the art that some amino acid sequence can be varied in a polypeptide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, thereby forming antibody conjugates.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

Using substantially the process of U.S. Pat. No. 6,180,357, the mouse monoclonal antibody 10A304.7 was obtained following immunization of mice with frozen single cell suspensions of the human HT-29 colon cancer cell line that had been grown as a solid tumor in SCID mice. These antibodies can be used in aid of staging and diagnosis of a cancer, and can be used to treat tumor metastases. The 10A304.7 antigen was expressed on the cell surface of a broad range of human cell lines from different tissue origins. The colon cancer cell line SW1116, the breast cancer cell lines MDA-MB-231, MCF-7, the prostate cancer cell line PC-3 and the ovarian cancer cell line OVCAR-3 were the cancer cell lines tested that were susceptible to the cytotoxic effects of 10A304.7 demonstrated in application Ser. No. 10/413,755, filed Apr. 14, 2003, now U.S. Pat. No. 6,794,494, issued Sep. 21, 2004.

The result of 10A304.7 cytotoxic activity against breast cancer cells in tissue culture was further extended by establishing its anti-tumor activity in vivo. In an in vivo model of human breast cancer, the MDA-MB-231 cancer cells were implanted underneath the skin at the scruff of the neck of severe combined immunodeficient (SCID) mice, as they are incapable of rejecting the human tumor cells due to a lack of certain immune cells. Pre-clinical xenograft tumor models are considered valid predictors of therapeutic efficacy. Xenografts in mice grow as solid tumors developing stroma, central necrosis and neo-vasculature in the same manner as naturally occurring cancers. The mammary tumor cell line MDA-MB-231 has been evaluated as an in vivo xenograft model in immunodeficient mice. The successful engraftment or 'take-rate' of MDA-MB-231 tumors and the sensitivity of the tumors to standard chemotherapeutic agents have characterized them as suitable models. The MDA-MB-231 parental cell line and variants of the cell line have been used successfully in xenograft tumor models to evaluate a wide range of therapeutic agents that are now used as clinical chemotherapeutic agents.

10A304.7 prevented tumor growth and reduced tumor burden in a in vivo model of human breast cancer. On day 56 post-implantation, 6 days after the last treatment dose, the mean tumor volume in the 10A304.7 treated group was 1 percent of the tumor volume in the isotype control treated group (p=0.0003, t-test). There were no clinical signs of toxicity throughout the study. Body weight measured at weekly intervals was a surrogate for health. There was no significant difference in body weight between the groups at the end of the treatment period (p=0.3512, t-test). Therefore 10A304.7 was well-tolerated and decreased the tumor burden in a breast cancer xenograft model.

In all, this invention teaches the use of the 10A304.7 antigen as a target for a therapeutic agent, that when administered can reduce the tumor burden of a cancer expressing the antigen in a mammal. This invention also teaches the use of CDMAB (10A304.7), and its derivatives, to target its antigen to reduce the tumor burden of a cancer expressing the antigen in a mammal. Furthermore, this invention also teaches the use of detecting the 10A304.7 antigen in cancerous cells that can be useful for the diagnosis, prediction of therapy, and prognosis of mammals bearing tumors that express this antigen.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies and/or a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

If a patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and an anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody-dependent cell-mediated cytotoxicity (ADCC) or complement-dependent cytotoxicity (CDC). For example murine IgM and IgG2a antibodies can activate human complement by binding the C-1 component of the complement system thereby activating the classical pathway of complement activation which can lead to tumor lysis. For human antibodies, the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody mediated cancer cell killing which are more widely accepted. The first is the use of antibodies as a vaccine to induce the body to produce an immune response against the putative antigen that resides on the cancer cell. The second is the use of antibodies to target growth receptors and interfere with their function or to down regulate that receptor so that effectively its function is lost.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137–143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39th Annual Meeting, 2003, pages 209–219).

Accordingly, it is an objective of the invention to utilize a method for producing CDMAB from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach CDMAB and antigen binding fragments thereof.

It is a further objective of the instant invention to produce CDMAB whose cytotoxicity is mediated through ADCC.

It is yet an additional objective of the instant invention to produce CDMAB whose cytotoxicity is mediated through CDC.

It is still a further objective of the instant invention to produce CDMAB whose cytotoxicity is a function of their ability to catalyze hydrolysis of cellular chemical bonds.

A still further objective of the instant invention is to produce CDMAB which are useful in a binding assay for the diagnosis, prognosis, and monitoring of cancer.

Other objects and advantages of this invention will become apparent from the following description wherein are set forth, by way of illustration and example, certain embodiments of this invention.

DETAILED DESCRIPTION OF THE INVENTION

EXAMPLE 1

Figure 1:
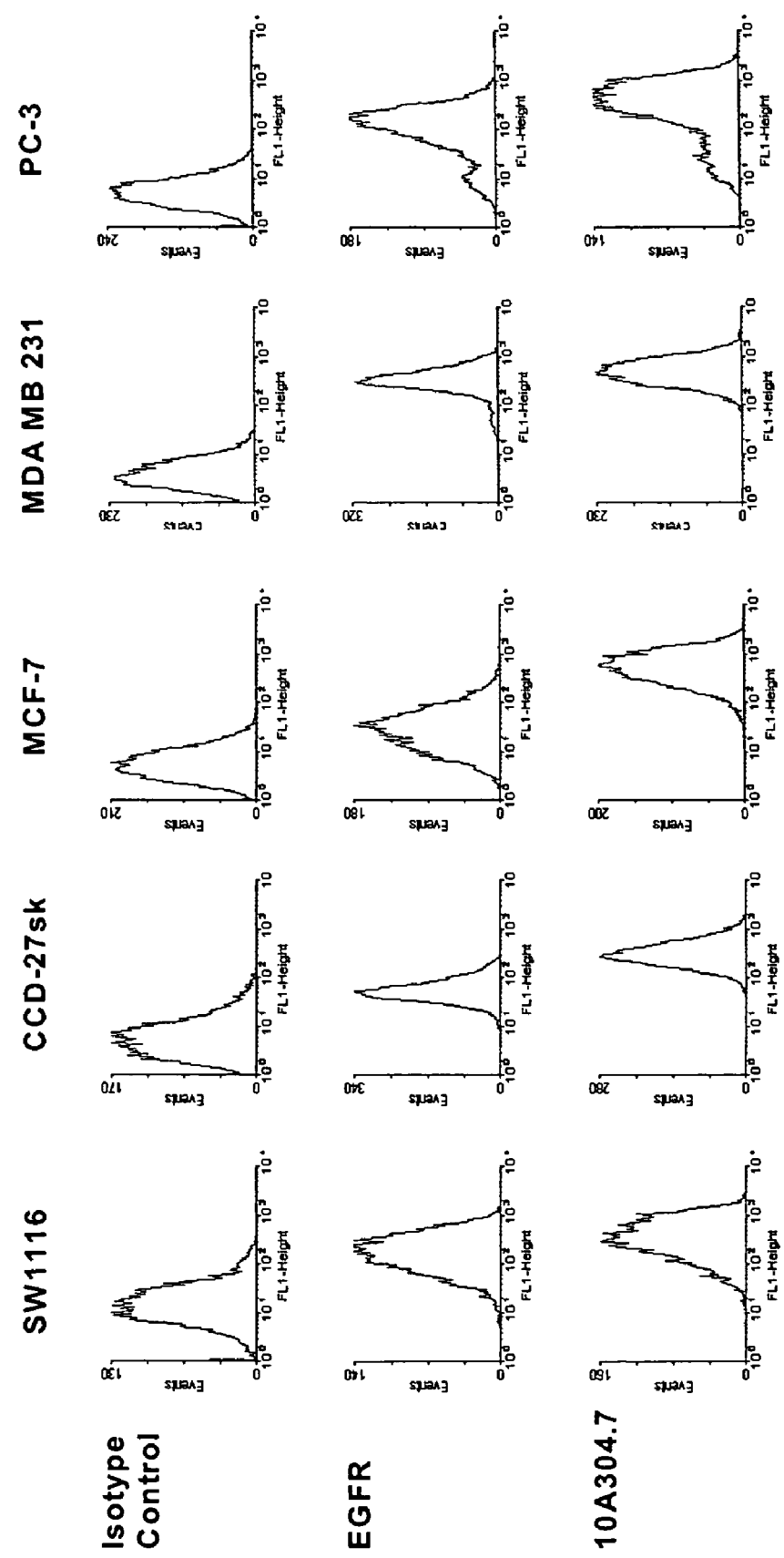
FIG. 1. Representative FACS histograms of 10A304.7, isotype control and anti-EGFR antibodies directed against several cancer and non-cancer cell lines.
Figure 2:
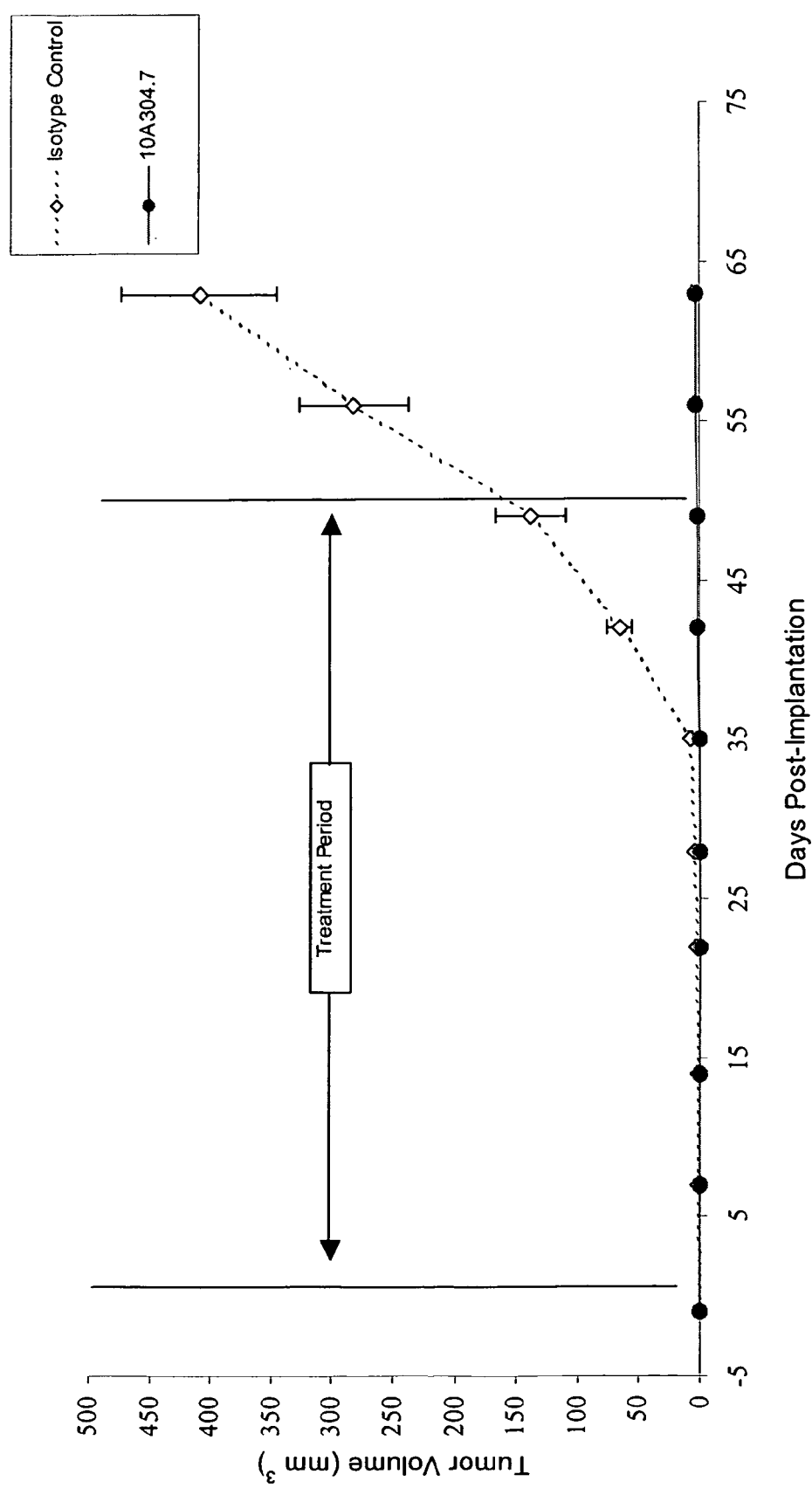
FIG. 2. Effect of 10A304.7 on tumor growth in a MDA-MB-231 breast cancer model. The dashed line indicates the period during which the antibody was administered. Data points represent the mean +/−SEM.
Figure 3:
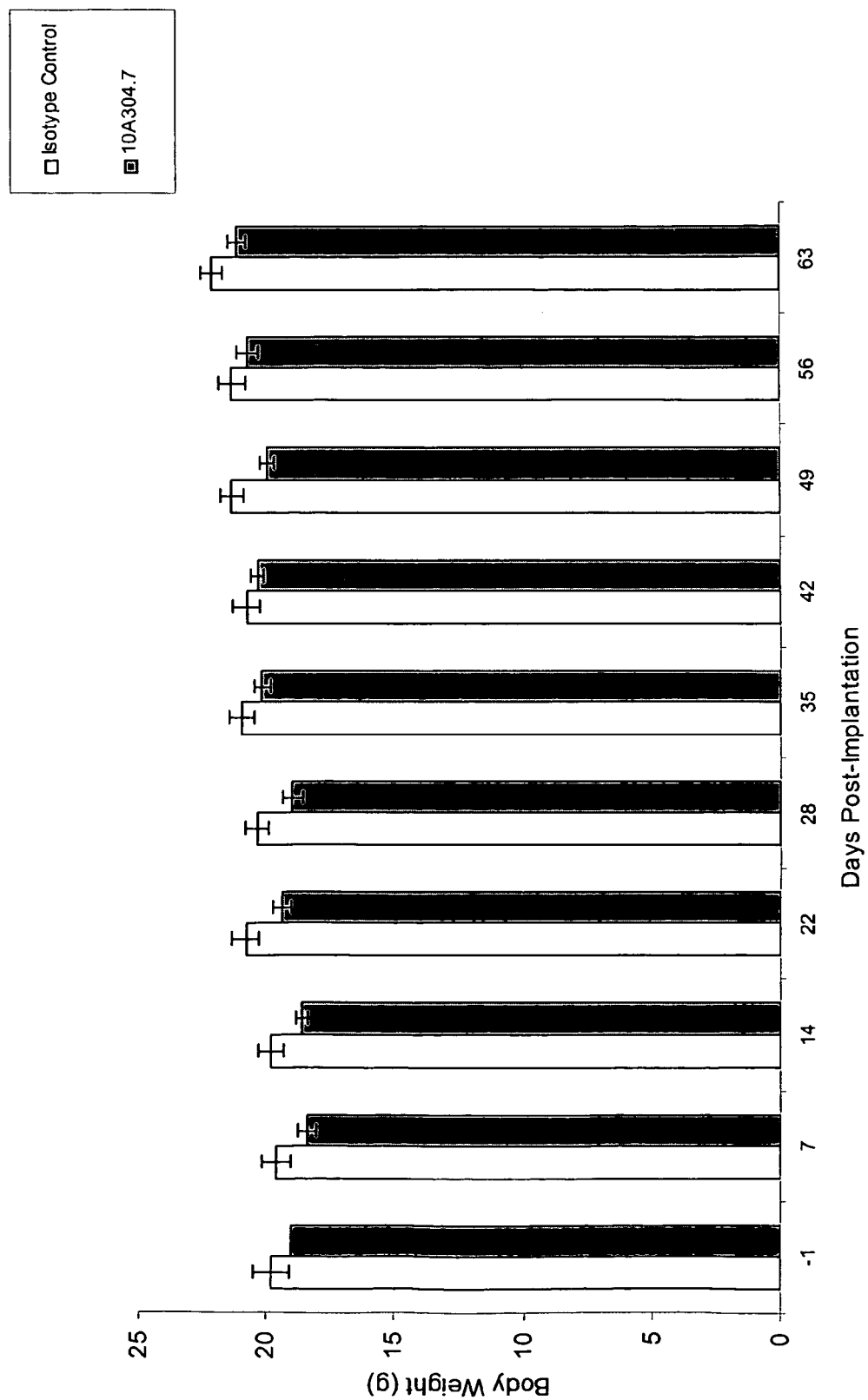
FIG. 3. Effect of 10A304.7 on body weight in a MDA-MB-231 breast cancer model. Data points represent the mean +/−SEM.

As shown in U.S. Pat. No. 6,794,494, the hybridoma cell line 10A304.7 was deposited, in accordance with the Budapest Treaty, with the American Type Culture Collection, 10801 University Blvd., Manassas, Va. 20110-2209 on Mar. 19, 2003, under Accession Number PTA-5065. In accordance with 37 CFR 1.808, the depositors assure that all restrictions imposed on the availability to the public of the deposited materials will be irrevocably removed upon the granting of a patent.

10A304.7 monoclonal antibody was produced by culturing the hybridoma in CL-1000 flasks (BD Biosciences, Oakville, ON) with collections and reseeding occurring twice/week and with purification according to standard antibody purification procedures with Protein G Sepharose 4 Fast Flow (Amersham Biosciences, Baie d'Urfé, QC).

As previously described in U.S. Pat. No. 6,794,494, 10A304.7 was compared to a number of both positive (anti-Fas (EOS9.1, IgM, kappa, 20 mg/mL, eBioscience, San Diego, Calif.), anti-Her2/neu (IgG1, kappa, 10 mg/mL, Inter Medico, Markham, ON), anti-EGFR (C225, IgG1, kappa, 5 mg/mL, Cedarlane, Hornby, ON), Cycloheximide (100 mM, Sigma, Oakville, ON), and $NaN_3$ (0.1%, Sigma, Oakville, ON)) and negative (107.3 (anti-TNP, IgG1, kappa 20 mg/mL, BD Biosciences, Oakville, ON), MPC-11 (antigenic specificity unknown, IgG2b, kappa 20 mg/mL), IgG Buffer (2%)) controls in a cytotoxicity assay (Table 1). Breast cancer (MDA-MB-231 (MB-231), MCF-7), colon cancer (Caco-2, DLD-1, Lovo, HT-29, SW 116, SW620), ovarian cancer (OVCAR), pancreatic cancer (BxPC-3), prostate cancer (PC-3), and non-cancer (CCD 27sk, Hs888.Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate density. After 2 days, 100 microliters of purified antibody was diluted into media, and then were transferred to the cell plates and incubated in a 5% $CO_2$ incubator for 5 days. The plate was then emptied by inverting and blotted dry. Room temperature DPBS containing $MgCl_2$ and $CaCl_2$ was dispensed into each well from a multichannel squeeze bottle, tapped three times, emptied by inversion and then blotted dry. 50 microliters of the fluorescent Live/Dead dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel and the results were tabulated in Table 1. The data represented an average of four experiments tested in triplicate and presented qualitatively in the following fashion: 4/4 experiments with 15% cytotoxicity above background (++++), 2/4 experiments with 15% cytotoxicity above background (+++), at least 2/4 experiments with 10–15% cytotoxicity above background (++), and at least 2/4 experiments with 8–10% cytotoxicity above background.

Unmarked cells in Table 1 represented inconsistent or effects less than the threshold cytotoxicity. The 10A304.7 antibody produced 35% of the cytotoxic effect of the well-described anti-EGFR antibody C225, which induced 31% cytotoxicity in the SW1116 colon cell line. Further, 10A304.7 induced significantly higher cytotoxicity against other cancer cells, compared with C225, including the breast cancer cell lines MDA-MB-231 (111%) and MCF-7 (850%), the prostate cancer cell line PC-3 (375%), and the ovarian cancer cell line OVCAR (667%). Importantly, 10A304.7 did not produce cytotoxicity against a number of non-cancer cells such as CCD 27sk or Hs888.Lu, indicating that the antibody has functional specificity towards various cancer cells. The chemical cytotoxic agents induced their expected cytotoxicity while a number of other antibodies which were included for comparison also performed as expected given the limitations of biological cell assays.

TABLE 1

| | Colon | | | | | | Pancreas | Breast | | Prostate | Ovary | Normal Cells | |
|---|---|---|---|---|---|---|---|---|---|---|---|---|---|
| | Caco-2 | DLD-1 | Lovo | HT-29 | SW1116 | SW620 | BxPC-3 | MB-231 | MCF-7 | PC-3 | OVCAR | CCD 27sk | Hs888.Lu |
| 10A304.7 (20 μg/mL) | | | | ++ | | | | ++ | ++++ | +++ | ++++ | | |
| Positive Controls | | | | | | | | | | | | | |
| Anti-Fas (20 μg/mL) | | ++ | ++++ | | | | ++++ | | | ++ | ++++ | | |
| Anti-Her2/neu (10 μg/mL) | | | | | | | | | | | | | |
| Anti-EGFR (c225, 5 μg/mL) | +++ | ++++ | | | ++++ | | | + | | | | | |
| Cycloheximide (100 μM) | ++++ | ++++ | ++++ | ++++ | ++++ | ++++ | ++++ | ++++ | ++++ | ++++ | ++++ | ++++ | ++++ |
| Negative Controls | | | | | | | | | | | | | |
| IgG1 (107.3, 20 μg/mL) | | + | | | | | | + | + | | | | |
| IgG2b (MPC-11, 20 μg/mL) | | + | | | | | | | | | | | |
| IgG Buffer (2%) | | | | | | | | | | | | | |

Also as previously described in U.S. Pat. No. 6,794,494, binding of 10A304.7 to the above-mentioned panel of cancer and normal cell lines was assessed by flow cytometry (FACS). Cells were prepared for FACS by initially washing the cell monolayer with DPBS (without $Ca^{++}$ and $Mg^{++}$). Cell dissociation buffer (INVITROGEN) was then used to dislodge the cells from their cell culture plates at 37° C. After centrifugation and collection the cells were resuspended in Dulbecco's phosphate buffered saline containing $MgCl_2$, $CaCl_2$ and 25% fetal bovine serum at 4° C. (wash media) and counted, aliquoted to appropriate cell density, spun down to pellet the cells and resuspended in staining media (DPBS containing $MgCl_2$, $CaCl_2$ and 2% fetal bovine serum) at 4° C. in the presence of test antibody (10A304.7) or control antibodies (isotype control, anti-EGF-R, or anti-Fas) at 20 micrograms/mL on ice for 30 minutes. Prior to the addition of Alexa Fluor 488-conjugated secondary antibody the cells were washed once with wash media. The Alexa Fluor 488-conjugated antibody in staining media was then added for 20 minutes. The cells were then washed for the final time and resuspended in staining media containing 1 microgram/mL propidium iodide. Flow cytometric acquisition of the cells was assessed by running samples on a FACScan using the CELLQUEST software (BD Biosciences). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform speak with a median fluorescent intensity of approximately 1–5 units. Live cells were acquired by gating for FSC and propidium iodide exclusion. For each sample, approximately 10,000 live cells were acquired for analysis and the results presented in Table 2.

Table 2 tabulated the mean fluorescence intensity fold increase above isotype control and is presented qualitatively as: less than 3 to 5 (+); 5 to 25 (++); 25 to 50 (+++); and above 50 (++++). Representative histograms of 10A304.7 antibody were compiled for FIG. 1 and evidence of the binding characteristics, inclusive of illustrated bimodal peaks in some cases. 10A304.7 non-specifically bound to all cell lines, including high binding to the non-cancer cells CCD 27sk and Hs888.Lu, but the degree of binding differed between the various cell lines. 10A304.7 thus selectively bound to the cell lines at different levels. Results from Tables 1 and 2 indicate that the binding of 10A304.7 to tumor cells is necessary for antibody-mediated cytotoxicity but it is not sufficient in triggering this event.

TABLE 2

| | Colon | | | | | | Pancreas | Breast | | Prostate | Ovary | Normal Cells | |
|---|---|---|---|---|---|---|---|---|---|---|---|---|---|
| | Caco-2 | DLD-1 | Lovo | HT-29 | SW1116 | SW620 | BxPC-3 | MB-231 | MCF-7 | PC-3 | OVCAR | CCD 27sk | Hs888.Lu |
| 10A304.7 | ++++ (bimodal) | ++ | +++ | ++++ | +++ | ++++ | +++ | ++++ | ++ | ++++ (bimodal) | ++++ | ++++ | ++++ |
| Anti-Fas | | ++ | ++ | ++ | + | | ++ | | | | ++ | ++ | +++ |
| Anti-EGFR | ++ | | ++ | +++ | ++ (bimodal) | | +++ | ++++ | ++ | +++ (bimodal) | +++ | ++ | +++ |

EXAMPLE 2

In Vivo MB-231 Tumor Experiments

With reference to FIGS. 2 and 3, 4 to 8 week old female SCID mice were implanted with 5 million MDA-MB-231 human breast cancer cells (MB-231) in 100 microliters saline injected subcutaneously in the scruff of the neck. The mice were randomly divided into 2 treatment groups of 5. On the day after implantation, 20 mg/kg of 10A304.7 test antibody or isotype control antibody (known not to bind MB-231 cells) was administered intraperitoneally at a volume of 300 microliters after dilution from the stock concentration with a diluent that contained 2.7 mM KCl, 1 mM $KH_2PO_4$, 137 mM NaCl and 20 mM $Na_2HPO_4$. The antibodies were then administered once per week for a period of 7 weeks in the same fashion. Tumor growth was measured about every seventh day with calipers for up to 10 weeks or until individual animals reached the Canadian Council for Animal Care (CCAC) end-points. Body weights of the animals were recorded for the duration of the study. At the end of the study all animals were euthanised according to CCAC guidelines.

10A304.7 prevented tumor growth and reduced tumor burden in a preventative in vivo model of human breast cancer. On day 56 post-implantation, 6 days after the last treatment dose, the mean tumor volume in the 10A304.7 treated group was 1 percent of the tumor volume in the isotype control treated group ($p=0.0003$, t-test, FIG. 2). There were no clinical signs of toxicity throughout the study. Body weight measured at weekly intervals was a surrogate for well-being and failure to thrive. There was no significant difference in body weight between the groups at the end of the treatment period ($p=0.3512$, t-test). Therefore 10A304.7 was well-tolerated and decreased the tumor burden in a breast cancer xenograft model.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of treating a colon, ovarian, prostate or breast tumor in a mammal, comprising administering to said mammal an isolated monoclonal antibody produced by the hybridoma deposited with the ATCC as accession number PTA-5065 or an antigen binding fragment produced from said isolated monoclonal antibody, in an amount effective to reduce said mammal's tumor burden.

2. The method of claim 1 wherein the antibody administered is a humanized antibody produced from the isolated monoclonal antibody produced by the hybridoma deposited with the ATCC under Accession Number PTA-5065, or is on antigen binding fragment of said humanized antibody.

3. The method of claim 1 wherein the antibody administered is a chimeric antibody produced from the isolated monoclonal antibody produced by the hybridoma deposited with the ATCC under Accession Number PTA-5065, or is an antigen binding fragment of said chimeric antibody.

4. The method of claim 1 or 2 or 3 wherein the antibody or antigen binding fragment administered is conjugated to a cytotoxic moiety.

5. The method of claim 4 wherein said cytotoxic moiety is a radioactive isotope.

6. The method of claim 1 or 2 or 3 wherein the antibody administered activates complement.

7. The method of claim 1 or 2 or 3 wherein the antibody administered mediates antibody dependent cellular cytotoxicity.

* * * * *